US00PP20101P2

(12) United States Plant Patent

Bergman

(10) Patent No.: US PP20,101 P2

(45) Date of Patent: Jun. 16, 2009

(54) *CHRYSANTHEMUM* PLANT NAMED 'YOHUDSON BAY'

(50) Latin Name: *Chrysanthemum×morifolium*
Varietal Denomination: Yohudson Bay

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/006,788

(22) Filed: Jan. 3, 2008

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

PP11,283 P * 3/2000 VandenBerg ..... Plt./286

* cited by examiner

*Primary Examiner*—S. B. McCormick Ewoldt
(74) *Attorney, Agent, or Firm*—C. A. Whealy

(57) ABSTRACT

A new and distinct cultivar of *Chrysanthemum* plant named 'Yohudson Bay', characterized by its compact, upright and uniformly mounded plant habit; freely branching habit; uniform flowering response; early flowering habit; daisy-type inflorescences with cherry red and yellow bi-colored ray florets; and excellent postproduction longevity.

2 Drawing Sheets

Botanical designation: *Chrysanthemum×morifolium.*
Cultivar denomination: 'Yohudson Bay'.

BACKGROUND OF THE INVENTION

The present invention relates to a new and distinct cultivar of *Chrysanthemum* plant, botanically known as *Chrysanthemum×morifolium,* commercially grown as a pot-type *Chrysanthemum* and hereinafter referred to by the name 'Yohudson Bay'.

The objective of the breeding program is to create new pot-type *Chrysanthemum* cultivars that are suitable for year-round production with uniform plant growth habit, freely branching habit, good vigor, desirable inflorescence form and floret colors, fast response time and excellent postproduction longevity.

The new *Chrysanthemum* originated from a cross-pollination made by the Inventor in February, 2003, in Salinas, Calif. of a proprietary selection of *Chrysanthemum× morifolium* identified as code number YB-A2579, not patented, as the female, or seed, parent with a proprietary selection of *Chrysanthemum×morifolium* identified as code number YB-5465, not patented, as the male, or pollen, parent. The new *Chrysanthemum* was discovered and selected by the Inventor as a single flowering plant within the progeny of the stated cross-pollination in a controlled environment in Fort Myers, Fla. in November, 2003. The selection of this plant was based on its uniform plant growth habit, freely branching habit, good vigor, desirable inflorescence form and floret coloration, fast response time and excellent postproduction longevity.

Asexual reproduction of the new *Chrysanthemum* by vegetative tip cuttings was first conducted in Fort Myers, Fla. in February, 2004. Asexual reproduction by cuttings has shown that the unique features of this new *Chrysanthemum* are stable and reproduced true to type in successive generations.

SUMMARY OF THE INVENTION

Plants of the cultivar Yohudson Bay have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yohudson Bay'. These characteristics in combination distinguish 'Yohudson Bay' as a new and distinct potted *Chrysanthemum* cultivar:

1. Compact, upright and uniformly mounded plant habit.
2. Freely branching habit.
3. Uniform flowering response.
4. Suitable for production as a center-budded or as natural spray type.
5. Early flowering habit, 7.5-week response time.
6. Daisy-type inflorescences with cherry red and yellow bicolored ray florets.
7. Excellent postproduction longevity with plants maintaining good substance and color for about four weeks in an interior environment.

Plants of the new *Chrysanthemum* differ from plants of the female parent selection in the following characteristics:

1. Plants of the new *Chrysanthemum* are more compact than and not as vigorous as plants of the female parent selection.
2. Plants of the new *Chrysanthemum* and the female parent selection differ in ray floret color as plants of the female parent selection have dark purple-colored ray florets.

Plants of the new *Chrysanthemum* differ from plants of the male parent selection primarily in ray floret color as plants of the male parent selection have cherry pink-colored ray florets. In addition, plants of the new *Chrysanthemum* do not produce pollen whereas plants of the male parent selection produce pollen.

Plants of the new *Chrysanthemum* can be compared to plants of the *Chrysanthemum* cultivar Yosun City, disclosed in U.S. Plant Pat. No. 17,460. In side-by-side comparisons conducted in Fort Myers, Fla., plants of the new *Chrysanthemum* differed from plants of the cultivar Yosun City in the following characteristics:

1. Plants of the new *Chrysanthemum* were more compact than plants of the cultivar Yosun City.
2. Plants of the new *Chrysanthemum* had broader ray florets than plants of the cultivar Yosun City.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of typical flowering plants of 'Yohudson Bay' grown in a container.

The photograph on the second sheet is a close-up view of a typical inflorescence of 'Yohudson Bay'.

DETAILED BOTANICAL DESCRIPTION

The aforementioned photographs and following observations and measurements describe plants grown in Leamington, Ontario, Canada during the autumn in a glass-covered greenhouse and under conditions and practices which approximate those generally used in commercial pot-type *Chrysanthemum* production. During the production of the plants, day temperatures ranged from 21° C. to 27° C., night temperatures ranged from 17° C. to 19° C. and light levels ranged from 4,000 to 6,000 foot candles. Four unrooted cuttings were directly stuck in 15-containers, exposed to long day/short night conditions, and pinched about three weeks later. At that time, the photoinductive short day/long night treatments were started. Plants used in the photographs and for the description were disbudded and were about two months old. In the following description, color references are made to The Royal Horticultural Society Colour Chart, 1995 Edition, except where general terms of ordinary dictionary significance are used.

Botanical classification: *Chrysanthemum×morifolium* cultivar Yohudson Bay.

Parentage:

*Female, or seed, parent.*—Proprietary selection of *Chrysanthemum×morifolium* identified as code number YB-A2579, not patented.

*Male, or pollen, parent.*—Proprietary selection of *Chrysanthemum×morifolium* identified as code number YB-5465, not patented.

Propagation:

*Type.*—Terminal vegetative cuttings.

*Time to initiate roots.*—About four days at temperatures of about 21° C.

*Time to produce a rooted young plant.*—About ten days at temperatures of about 21° C.

*Root description.*—Medium thickness, fibrous; white in color.

*Rooting habit.*—Freely branching; moderately dense.

Plant description:

*Appearance.*—Herbaceous daisy pot-type *Chrysanthemum* typically grown as a center-budded or as a natural spray type. Stems upright and outwardly spreading giving a uniformly mounded appearance to the plant. Freely branching habit, about four lateral branches develop after removal of terminal apex (pinching), dense and full plant habit. Compact growth habit.

*Plant height.*—About 28.5 cm.

*Plant width.*—About 38 cm.

*Lateral branches (peduncles).*—Length: About 24 cm. Diameter: About 6.5 mm. Internode length: About 1.6 cm. Strength: Strong. Texture: Pubescent. Color: Close to 146A.

Foliage description:

*Arrangement.*—Alternate, simple.

*Length.*—About 8.7 cm.

*Width.*—About 5.9 cm.

*Apex.*—Mucronate.

*Base.*—Attenuate with truncate tendencies.

*Margin.*—Palmately lobed, sinuses between lateral lobes parallel to slightly convergent.

*Texture, upper and lower surfaces.*—Fine pubescence; veins prominent on lower surface.

*Color.*—Developing and fully expanded foliage, upper surface: Close to 147A; venation, close to 147B. Developing and fully expanded foliage, lower surface: Close to 147B; venation, close to 147B.

*Petiole length.*—About 1.7 cm.

*Petiole diameter.*—About 3.5 mm.

*Petiole color, upper and lower surfaces.*—Close to 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Inflorescence not fragrant. Typically grown as a center-budded or natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about 7.5 weeks later.

*Postproduction longevity.*—Inflorescences maintain good color and substance for about four weeks in an interior environment.

*Quantity of inflorescences per lateral stem.*—About nine to ten.

*Inflorescence bud.*—Height: About 4 mm. Diameter: About 7 mm. Shape: Oblate. Color: Between 138A and 141A.

*Inflorescence size.*—Diameter: About 8.5 cm. Depth (height): About 1.5 cm. Disc diameter: About 1.75 cm. Receptacle height: About 6 mm. Receptacle diameter: About 6 mm. Receptacle color: Close to 144A.

*Ray florets.*—Shape: Elongated oblong. Orientation: Initially upright, eventually outwardly arching. Length: About 4.2 cm. Width: About 1.1 cm. Corolla tube length: About 4 mm. Apex: Emarginate or acute. Base: Attenuate. Margin: Entire. Texture, upper and lower surfaces: Smooth, glabrous, satiny. Number of ray florets per inflorescence: About 32 arranged in about two whorls. Color: When opening, upper and lower surfaces: Ground color, close to 9A; longitudinal stripes and towards the apex, overlain with close to 53A. Color does not fade with development. Fully opened, upper and lower surfaces: Ground color, close to 6D; longitudinal stripes and towards the apex, underlain with close to 59A.

*Disc florets.*—Arrangement: Massed at center of receptacle. Shape: Tubular, elongated. Apex: Five-pointed. Length: About 7.5 mm. Width, at the apex: About 2 mm. Width, at the base: About 1.5 mm. Number of disc florets per inflorescence: About 172. Color, immature: Apex: Close to N144A. Mid-section: Close to 145D. Base: Close to 145D. Color, mature: Apex: Close to 12A. Mid-section: Close to 145D. Base: Close to 155D.

*Phyllaries.*—Number of phyllaries per inflorescence: About 20 arranged in about two whorls. Length: About 8 mm. Width: About 4 mm. Shape: Lanceolate. Apex: Acute. Base: Truncate. Texture, upper surface: Smooth, waxy. Texture, lower surface: Pubescent. Color, upper surface: Close to 137A to 137B. Color, lower surface: Close to 137A.

*Peduncles.*—Length: First peduncle: About 2.6 cm. Fourth peduncle: About 5.3 cm. Seventh peduncle: About 4.9 cm. Diameter (first peduncle): About 2.5 mm. Angle: About 45° from vertical. Strength: Strong, flexible. Texture: Pubescent. Color: Close to 146A.

*Reproductive organs.*—Androecium: Present on disc florets only. Filament length: About 4 mm. Filament color: Close to 154D. Anther shape: Narrowly oblong. Anther length: About 1 mm. Anther color: Close to 12A. Pollen amount: None observed. Gynoecium: Pistil length: About 6 mm. Stigma shape: Bi-parted. Stigma color: Close to 13A. Style length: About 4 mm. Style color: Close to 6D. Ovary color: Close to 154D.

*Seed/fruit.*—Seed and fruit production have not been observed.

Disease/pest resistance: Resistance to pathogens and pests common to *Chrysanthemums* has not been observed on plants grown under commercial conditions.

Temperature tolerance: Plants of the new *Chrysanthemum* have been observed to tolerate temperatures ranging from about 1° C. to about 38° C.

It is claimed:

1. A new and distinct *Chrysanthemum* plant named 'Yohudson Bay' as illustrated and described.

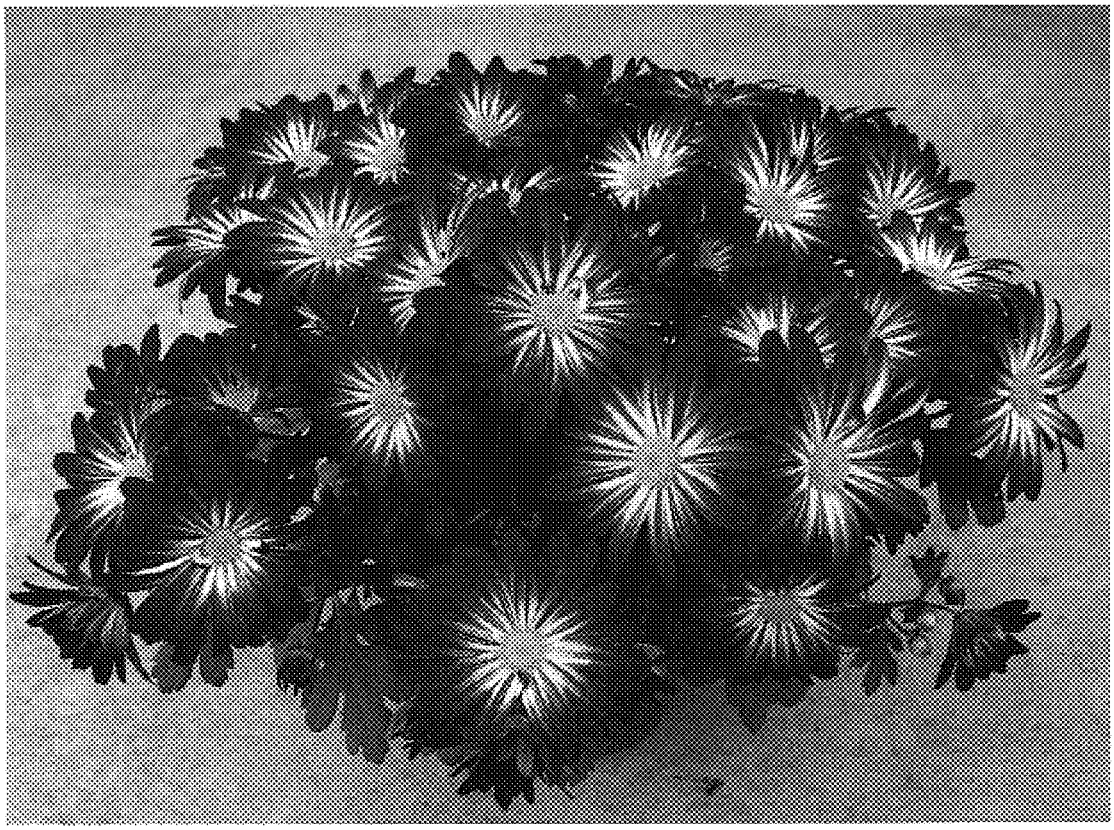

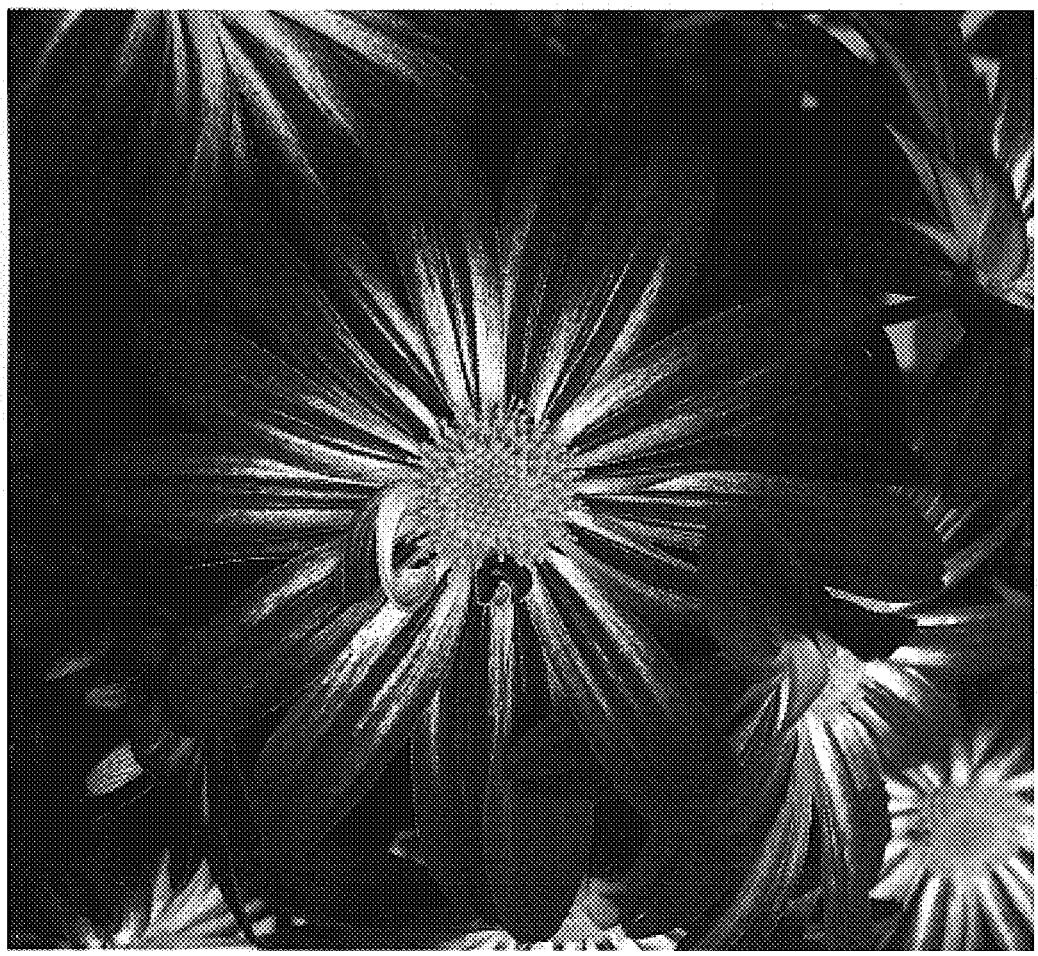

* * * * *